(12) United States Patent
Heiman

(10) Patent No.: US 9,205,042 B1
(45) Date of Patent: Dec. 8, 2015

(54) LIP AND SKIN CARE PRODUCT, DISPENSER AND METHODS

(71) Applicant: Robert Heiman, Reno, NV (US)

(72) Inventor: Robert Heiman, Reno, NV (US)

( * ) Notice: Subject to any disclaimer, the term of this patent is extended or adjusted under 35 U.S.C. 154(b) by 297 days.

(21) Appl. No.: 13/731,424

(22) Filed: Dec. 31, 2012

(51) Int. Cl.
| | |
|---|---|
| *A61K 35/644* | (2015.01) |
| *A61K 36/61* | (2006.01) |
| *A61K 36/886* | (2006.01) |
| *A61K 36/28* | (2006.01) |
| *A61K 9/00* | (2006.01) |
| *A45D 34/04* | (2006.01) |
| *A61K 31/01* | (2006.01) |
| *A61K 31/045* | (2006.01) |
| *A61K 31/125* | (2006.01) |

(52) U.S. Cl.
CPC ............ *A61K 9/0014* (2013.01); *A45D 34/041* (2013.01); *A61K 31/01* (2013.01); *A61K 31/045* (2013.01); *A61K 31/125* (2013.01); *A61K 35/644* (2013.01); *A61K 36/28* (2013.01); *A61K 36/61* (2013.01); *A61K 36/886* (2013.01)

(58) Field of Classification Search
USPC .......................................... 424/725, 539, 744
IPC .............................. A61K 36/61,35/644, 36/886
See application file for complete search history.

(56) References Cited

U.S. PATENT DOCUMENTS

| | | | | |
|---|---|---|---|---|
| 6,197,305 | B1 * | 3/2001 | Friedman et al. ............. | 424/737 |
| 2003/0003140 | A1 * | 1/2003 | Domb et al. .................. | 424/449 |
| 2006/0051339 | A1 * | 3/2006 | Sivak ............................ | 424/94.6 |
| 2006/0088612 | A1 * | 4/2006 | Sivak et al. ................... | 424/745 |
| 2006/0165620 | A1 * | 7/2006 | Bujard et al. .................. | 424/63 |
| 2008/0003052 | A1 * | 1/2008 | Lee et al. ...................... | 401/209 |
| 2010/0092413 | A1 * | 4/2010 | Bellman ........................ | 424/59 |
| 2011/0244039 | A1 * | 10/2011 | Domb et al. .................. | 424/464 |

FOREIGN PATENT DOCUMENTS

| | | | |
|---|---|---|---|
| CN | 102366426 | * | 3/2012 |
| DE | 202008007376 | * | 11/2008 |
| KR | 1084489 | * | 11/2011 |
| WO | WO 01/66079 | * | 9/2001 |
| WO | WO 2012/035478 | * | 3/2012 |

* cited by examiner

*Primary Examiner* — Chris R Tate
(74) *Attorney, Agent, or Firm* — Elie Gendloff; TechLaw LLP

(57) ABSTRACT

A lip and skin care product that is essentially devoid of petroleum products, is liquid at temperatures from 28 to 206 degrees Fahrenheit, and comprises in excess of 3 weight percent propolis and in excess of 1 weight percent tea tree oil, and is applied from a dispenser made of a material that is inert with respect to the active ingredients of tea tree leaf oil and propolis.

1 Claim, 1 Drawing Sheet

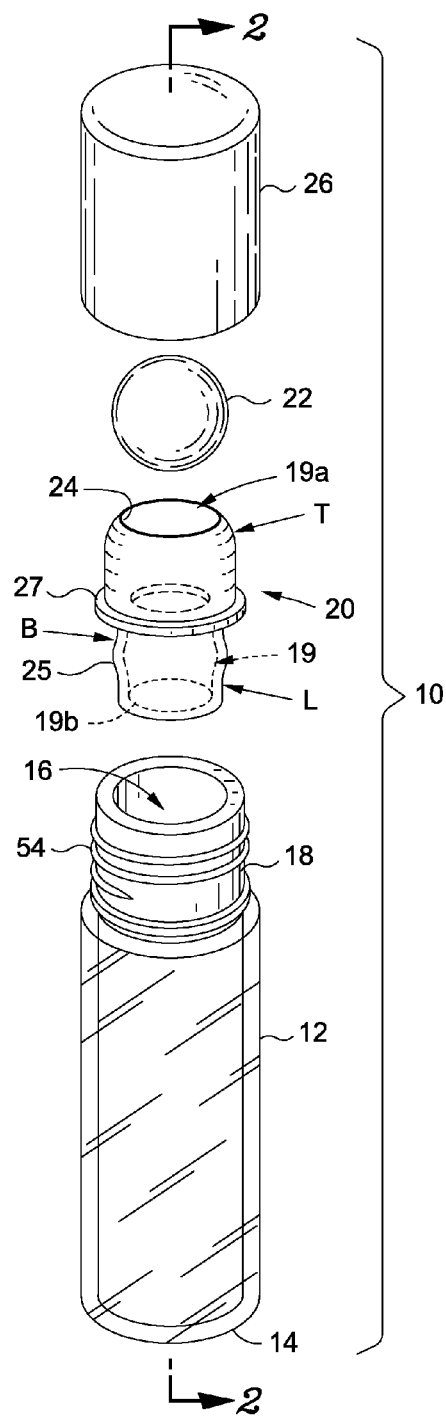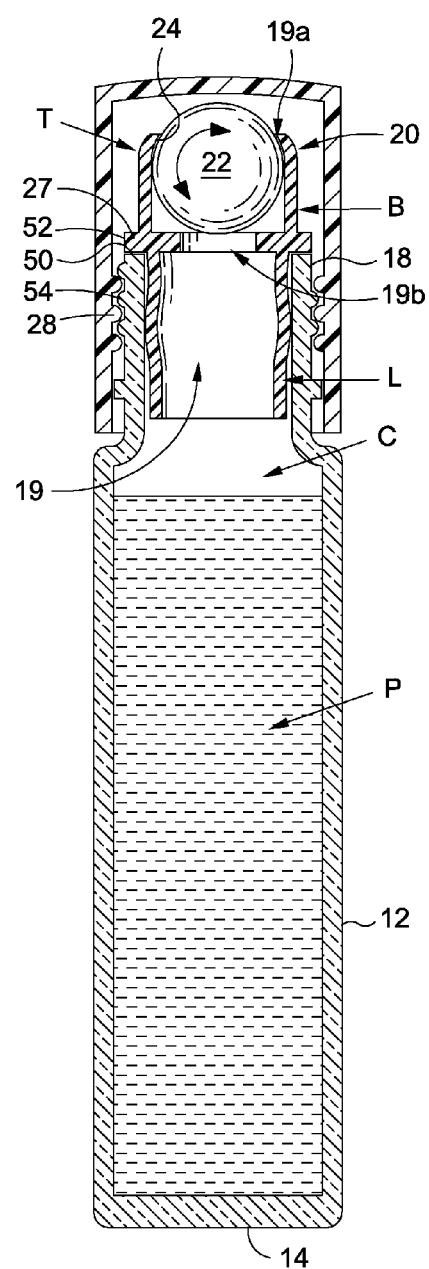
Fig. 1
Fig. 2

LIP AND SKIN CARE PRODUCT, DISPENSER AND METHODS

INCORPORATION BY REFERENCE

Any and all U.S. patents, U.S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "substantially" and "essentially" have equivalent meanings.

BACKGROUND

Chapped lips and skin is a condition that is typically treated with lip moisturizers comprising mainly a waxy material, typically a petroleum product that melts in hot weather and becomes hard in cold weather. Such prior art lip moisturizers merely attempt to disguise chapped lips and/or make the chapped lips feel better through the use of a waxy base or another petroleum product. They do not eliminate the cause of the problem. Conventional products used for cold sores and fever blisters attempt to soften the sore or temporarily relieve the discomfort without eliminating the cause. Products currently on the market lay on the surface of the lip, creating a coating of wax and oil for the purpose of moisturizing. This waxy-oily layer inhibits the natural process of exfoliation of chapped, dried or infected cells.

SUMMARY

My lip and skin care product eliminates or suppress the biological agents that cause cold sores, and it protects the lips and skin from an environment that allows chapped lips to occur. My lip and skin care product, dispenser and methods have one or more of the features depicted in the embodiment discussed in the section entitled "DETAILED DESCRIPTION OF ONE ILLUSTRATIVE EMBODIMENT." The claims that follow define my lip and skin care product, dispenser and methods, distinguishing them from the prior art; however, without limiting the scope of my lip and skin care product, dispenser and method as expressed by these claims, in general terms, some, but not necessarily all, of their features are:

One, my lip and skin care product comprises a mixture of from 3 to 10 weight percent propolis and from 1 to 4 weight percent tea tree leaf oil and the balance a solvent, for example, an alcohol. Propolis is a red or brown resinous substance collected by honeybees from tree buds, used by them to fill crevices and to seal and varnish honeycombs. Brazilian rainforest propolis has been found to be the best. The tea tree leaf oil also identified as *Melaleuca Alternifolia* (tea tree) leaf oil. The propolis and tea tree leaf oil are active ingredients that create a deadly environment for virus, bacteria and fungus while at the same time creating a stimulating and healthy environment for normal cells. High percentages of propolis (in excess of 3 weight percent) and tea tree oil create (in excess of 1 weight percent) provide an anti-bacterial, anti-viral, anti-fungal and anti-inflammatory environment to prohibit the growth of diseased tissues. My lip and skin care product has anti-inflammatory and analgesic properties and is an excellent application for insect bites, itching, scratching and irritated cells anywhere on the body.

My product is a liquid at temperatures from 28 to 206 degrees Fahrenheit, and consequently, can be used with my unique dispenser. Other optional ingredients, such as, for example, the chemicals listed below in the TABLE OF INGREDIENTS, may be included. Of these optional ingredients isododecane, sunflower seed oil, aloe vera oil, camphor, and methanol are the most useful. Unlike prior art products, my lip and skin care product isolates and separates damaged cells from healthy cells and accelerates their exfoliation; it breaks down and destroys the herpes simplex viral spores that can germinate into a cellular, viral infection; it appears to accelerate the body's natural DNA self-destruct mechanism that causes the breakdown of a non-functional cell that is damaged or infected; it rapidly breaks down herpes simplex cold sores/fever blisters and speeds up the exfoliation of the damaged cells and has the ability to prevent a reoccurrence of the cold sore infection when used as a natural moisturizer; it speeds up the body's natural self destruct process of dried, chapped skin cells and accelerates the regeneration of healthy new replacement cells; it accelerates the body's natural breakdown process of Herpes Simplex Type 1 cold sores/fever blisters and prevents their reoccurrence by breaking down the spores that are attached to nerve endings that can germinate into a fully active herpes simplex virus 1 or 2. My lip and skin care product is equally effective for the cure and prevention of eruptions of Herpes Simplex Type 2 virus, and diminishes outbreaks of Herpes Simplex occurring cold sores/fever blisters and can prevent their reoccurring.

Two, my lip and skin care product is unique in that is essentially devoid of any petroleum product. It may include isododecane, which is a mixture of highly branched C12 isoparaffins, mainly the 2,2,4,6,6-pentamethylheptane isomer, and sunflower oil. These two ingredients are emollients and they accelerate the body's natural exfoliation process, eliminating exposed dried, chapped, infected, dying or dead cells and delivers a curing process with occasional reapplication. Other non-petroleum ingredients may be included in my lip and skin care product, for example, butters, vitamins, peptides and enzyme proteins.

Three, my method of treating chapped lips and skin comprises applying to the lips or skin my product. Because my product contains no wax and is a penetrating liquid, it stimulates healing of chapped, dried and/or infected cells of the lips without leaving a residual wax coating. My method of treating chapped lips and skin results in healthier cells in all layers of the skin, allowing surface capillaries to provide a natural healthy color and youthful glow. Regular use of my lip and skin care product creates an environment for rapid healing of persistent cracked lips resulting from bacteria accumulated at the corners of the mouth. It gives superior protection against chapped and cracked lips caused by severe weather and salt water, is soothing and effective relief for children who develop chapped lips from persistent licking of the lips and adjacent areas to their mouth.

Four, my lip and skin care product dispenser comprises a chamber holding my lip and skin care product. Consequently, my dispenser has an applicator head in fluid communication with the chamber for the delivery of my liquid lip and skin care product to the lips or skin of a user. Because my product is a liquid, it easily flows from the chamber to the applicator head, regardless of the ambient temperature being hot or cold. Active ingredients of tea tree oil and propolis in excess of 3.5 weight percent (3.5%) will dissolve most plastics. Therefore, my lip and skin care product requires that it be delivered in a dispenser that avoids chemical reaction with the active ingredients of tea tree oil and propolis. In other words, the material comprising the dispenser is inert with respect to the active ingredients of tea tree oil and propolis. In one embodiment, the chamber is made from glass and the applicator head is a steel ball seated in a raceway made of a plastic such as high density polypropylene that resist attack by the active ingredients of my product.

Five, my method of making a lip and skin care product comprising the steps of mixing propolis with a solvent and heating this mixture at a temperature substantially from 101 to 105 degrees Fahrenheit for a sustained substantially continuous period in excess of 24 hours. After the heating period, the hot mixture is filtered and cooled to a lower temperature that is no less than 100 degrees Fahrenheit. The other ingredients of my lip and skin care product are added to the cooled, filtered mixture. The solvent may be ethyl alcohol and comprises substantially from 35 to 65 weight percent of the mixture of propolis and the solvent.

These features are not listed in any rank order nor is this list intended to be exhaustive.

DESCRIPTION OF THE DRAWING

On embodiment of my dispenser is discussed in detail in connection with the accompanying drawing, which is for illustrative purposes only. This drawing includes the following figures (Figs.), with like numerals indicating like parts:

FIG. 1 is an exploded perspective view of one embodiment of my dispenser.

FIG. 2 is a cross-sectional view taken along line 2-2 of FIG. 1.

DETAILED DESCRIPTION OF ONE ILLUSTRATIVE EMBODIMENT

My liquid lip and skin care product P (FIG. 2) is a liquid and will not melt or freeze under normal ambient conditions, is petro-chemical free, and includes a mixture of active ingredients propolis and tea tree leaf oil as discussed above. As illustrated in FIGS. 1 and 2, my dispenser 10 comprises a glass, cylindrically shaped bottle 12 and a cap 26 screwed onto a neck section 18 of the bottle, retaining my liquid lip and skin care product P within the bottle 12 until the cap is removed. The bottle 12 has a closed bottom 14 and its hollow interior forms a chamber C holding my liquid lip and skin care product P. Inserted through a circular entrance opening 16 into the threaded neck section 18 is an applicator head 20, sealing the opening 16 so my liquid lip and skin care product P may only exit the chamber C through the applicator head 20. The neck section 18 includes threads 54 surrounding the circular entrance opening 16 that engage a threaded interior 28 at the entry to the cap 26.

The applicator head 20 is a unitary, integral, single piece molded plastic made of a material that does not react with the active ingredients tea tree oil and propolis. It includes a substantially cylindrical body B that has a passageway 19 extending from a circular opening 19a in a top section T of the body B to an exit opening 19b in a lower section L of the body, a raceway 24 forming an upper wall of the top section in which is seated snugly a stainless steel ball 22, and a large diameter circular stop ring 27 on the exterior of the body intermediate the top opening 19a and the exit opening 19b. The lower section L has an enlarged section diameter slightly greater than that of the opening 16 so the applicator head 20 fits snug within the opening 16 of the neck section 18 upon insertion of the lower section L into the opening 16. The stop ring 27 limits the inward movement of the applicator head 20 so that the stop ring abuts the circular ledge 50 upon insertion of the applicator head.

As shown in FIG. 2, the dimensions of the components of the applicator head 20 and the bottle 12 are such that, upon screwing the cap 26 to the neck section 18, an outer edge 52 of the stop ring 27 is substantially aligned with, or inward of, the bottle's threads 54 surrounding the opening 16. The stainless steel ball 22 is mounted to rotate in any direction within the raceway 24. The stop ring 27 has an enlarged diameter greater than the diameter of the open top 16 so the ring acts as a stop element to limit the inward movement of the applicator head 20 as the plug section 25 is pushed into the open top 16. Inverting the bottle 12 with the cap 26 removed brings my liquid lip and skin care product P from the chamber C into fluid communication with the stainless steel ball 22. Upon contact with a user's lips or skin and moving the ball 22 while in contact with the lips or skin, collects the product P on the surface of the ball, and with contact, is released onto the user's lips or skin.

| TABLE OF INGREDIENTS | | | |
|---|---|---|---|
| Wt. Percent | Ingredient (INCI Name) | Function | CAS No. |
| 30.00-50.00 | Isododecane | Emollient | 141-70-8 |
| 10.00-15.00 | Helianthus Annuus (Hybrid Sunflower Seed) Oil | Emollient | 164250-88-8 |
| 3.00-10.00 | Bee Propolis Extract | Emollient | No CAS # |
| 3.00-10.00 | Aloe Barbadensis (Aloe Vera) Oil | Emollient | 100084-89-7 |
| 1.00-4.00 | Melaleuca Alternifolia (Tea Tree) Leaf Oil | Emollient | 68647-73-4 |
| 0.30-1.00 | Menthol (Analgesic) | Antiseptic | 89-78-1 |
| 0.10-0.30 | Tocopherol (Antioxidant) | Antioxidant | 59-02-9 |
| 0.01-0.10 | Camphor (OTC) | Antiseptic | 76-22-2 |
| 0.01-0.10 | Vaccinium Macrocapon (Cranberry) Fruit Juice | Botanical | 91770-88-6 |
| 0.01-0.10 | Beeswax | Thickener | 8006-40-4 |
| 0.01-0.10 | Zinc Sulfate | Stimulant | 7446-19-7 |
| 0.01-0.10 | Vitis Vinifera (Grape) Seed Oil | Botanical | 8024-22-4 |
| 0.01-0.10 | Usnea Barbata (Lichen) Extract | Botanical | 84696-53-7 |
| 0.01-0.10 | Theobroma Cacao (Cocoa) Seed Butter | Emollient | 8002-31-1 |
| 0.01-0.10 | Sambucus Nigra (Elder Flower) Extract | Botanical | 84603-58-7 |
| 0.01-0.10 | Phenol (Analgesic) | Emollient | 108-95-2 |
| 0.01-0.10 | Persea Gratissima (Avocado) Oil Unsaponifiables | Emollient | 91770-40-0 |

-continued

TABLE OF INGREDIENTS

| Wt. Percent | Ingredient (INCI Name) | Function | CAS No. |
|---|---|---|---|
| 0.01-0.10 | Ozokerite Wax | Thickener | 12198-93-5 |
| 0.01-0.10 | Larrea Divaricata (Chapparel) Extract | Botanical | No CAS # |
| 0.01-0.10 | Hydrastis Canadensis (Golden Seal) Extract | Botanical | 84603-60-1 |
| 0.01-0.10 | Hamamelis Virginiana (Witch Hazel) | Astringent | 68916-39-2 |
| 0.01-0.10 | Glycyrrhiza Glabra (Licorice) Extract | Botanical | 97686-23-8 |
| 0.01-0.10 | Copernicia Cerifera (Carnauba) Wax | Thickener | 8015-86-9 |
| 0.01-0.10 | Commiphora Myrrha (Myrrh) Extract | Botanical | No CAS # |
| 0.01-0.10 | Citrus Medica Limonum (Lemon) Fruit Extract | Botanical | 84929-31-7 |
| 0.01-0.10 | Butyrospermum Parkii (Shea Butter) | Emollient | 91080-23-8 |
| 0.01-0.10 | Boric Acid | Acidifier | 10043-35-3 |
| 0.01-0.10 | Ascorbyl Palmitate (Vitamin C Palmitate) | Vitamin | 137-66-6 |
| 0.01-0.10 | Aleurites Moluccana Seed (Kukui Nut) Oil | Emollient | 8015-80-3 |
| 0.01-0.10 | Octyldodecanol | Emollient | 5333-42-6 |
| 0.01-0.10 | Hydrolyzed Elastin | Humectant | 73049-73-7 |
| 0.01-0.10 | Butyrospermum Parkii (Shea Butter) Fruit | Emollient | 194043-92-0 |
| 0.01-0.10 | Retinyl Palmitate (Vitamin A Palmitate) | Vitamin | 79-81-2 |
| 0.01-0.10 | Cholecalciferol (Vitamin D3) | Vitamin | 67-97-0 |
| 0.01-0.10 | Aloe Barbadensis (Aloe Vera) Leaf Juice | Botanical | 8001-97-6 |
| 0.01-0.10 | Rubus Idaeus (ORGANIC Raspberry) Juice | Botanical | 8027-46-1 |
| 0.01-0.10 | Niacin (Nicotinic Acid) | Vitamin | 59-67-6 |
| 0.01-0.10 | Riboflavin (Vitamin B2) | Vitamin | 83-88-5 |
| 0.01-0.10 | Biotin (Vitamin B7) | Vitamin | 58-85-5 |
| 0.01-0.10 | Coco-Caprylate/Caprate | Emollient | No CAS # |

Method of Manufacture

The propolis is blended with a solvent such as ethyl alcohol (about 35-65 weight percent grain alcohol) and heated at a temperature of 140 degrees Fahrenheit for a sustained, continuous period of 4 days with mixing. When the propolis is completely dissolved in the alcohol, the mixture is filtered through a nylon sock. The mixture is cooled to about 100 degrees Fahrenheit and the tree leaf oil and other ingredients are added.

SCOPE OF THE INVENTION

The above presents a description of the best mode I contemplate of carrying out my lip and skin care product, dispenser and method, and of the manner and process of making and using them, in such full, clear, concise, and exact terms as to enable a person skilled in the art to make and use. My lip and skin care product, dispenser and method are, however, susceptible to modifications and alternate constructions from the illustrative embodiment discussed above which are fully equivalent. Consequently, it is not the intention to limit my lip and skin care product, dispenser and method to the particular embodiment disclosed. On the contrary, my intention is to cover all modifications and alternate constructions coming within the spirit and scope of my lip and skin care product, dispenser and method as generally expressed by the following claims, which particularly point out and distinctly claim the subject matter of my invention:

The invention claimed is:
1. A lip and skin care product comprising a mixture of from
3 to 10 weight percent propolis,
1 to 4 weight percent tea tree leaf oil,
30 to 50 weight percent isododecane,
3 to 10 weight percent aloe vera oil,
10 to 15 weight percent sunflower seed oil,
0.01 to 0.10 weight percent camphor,
0.30 to 1.0 weight percent menthol, and
the balance ethyl alcohol.

* * * * *